(12) United States Patent
Martin et al.

(10) Patent No.: US 6,303,365 B1
(45) Date of Patent: Oct. 16, 2001

(54) METHOD OF DETERMINING ACTIVITY OF 1-DEOXY-D-XYLULOSE-5-PHOSPHATE REDUCTOISOMERASE AND 1-DEOXY-D-XYLULOSE-5-PHOSPHATE SYNTHASE

(75) Inventors: William Frank Martin, Neuss; Ruediger Hain; Klaus-Guenther Tietjen, both of Langenfeld; Marco Busch, Burscheid, all of (DE); Andreas S. Kloti, Durham, NC (US)

(73) Assignees: Paradigm Genetics, Inc. R.T.P, NC (US); Bayer Ag, Leverkusen (DE)

( * ) Notice: Subject to any disclaimer, the term of this patent is extended or adjusted under 35 U.S.C. 154(b) by 0 days.

(21) Appl. No.: 09/449,335

(22) Filed: Nov. 24, 1999

(30) Foreign Application Priority Data

Jul. 30, 1999 (DE) .............................................. 199 35 967

(51) Int. Cl.[7] .............................. C12N 1/20; C12N 15/00; C07H 21/04
(52) U.S. Cl. .................................... 435/252.3; 435/320.1; 435/325; 536/23.2
(58) Field of Search ................................. 435/233, 320.1, 435/252.3, 325; 536/23.2

(56) References Cited

PUBLICATIONS

Fleischmann et al., Database Swiss prot–39, accession No. P44055, Nov. 1995.*

Schwender et al., FEBS Lett., 455(1–2), 140–144, Aug. 1999.*

* cited by examiner

*Primary Examiner*—Rebecca E. Prouty
*Assistant Examiner*—Maryam Monshipouri
(74) *Attorney, Agent, or Firm*—Joseph T. Majka; Elaine T. Sale; Sorojini J. Biswas

(57) ABSTRACT

The invention relates to DNA which encodes Arabidopsis 1-deoxy-xylulose-5-phosphate reductoisomerase and to a method of identifying modulators of the 1-deoxy-D-xylulose-5-phosphate reductoisomerase and 1-deoxy-D-xylulose-5-phosphate synthase activity.

13 Claims, 1 Drawing Sheet

Figure 1:
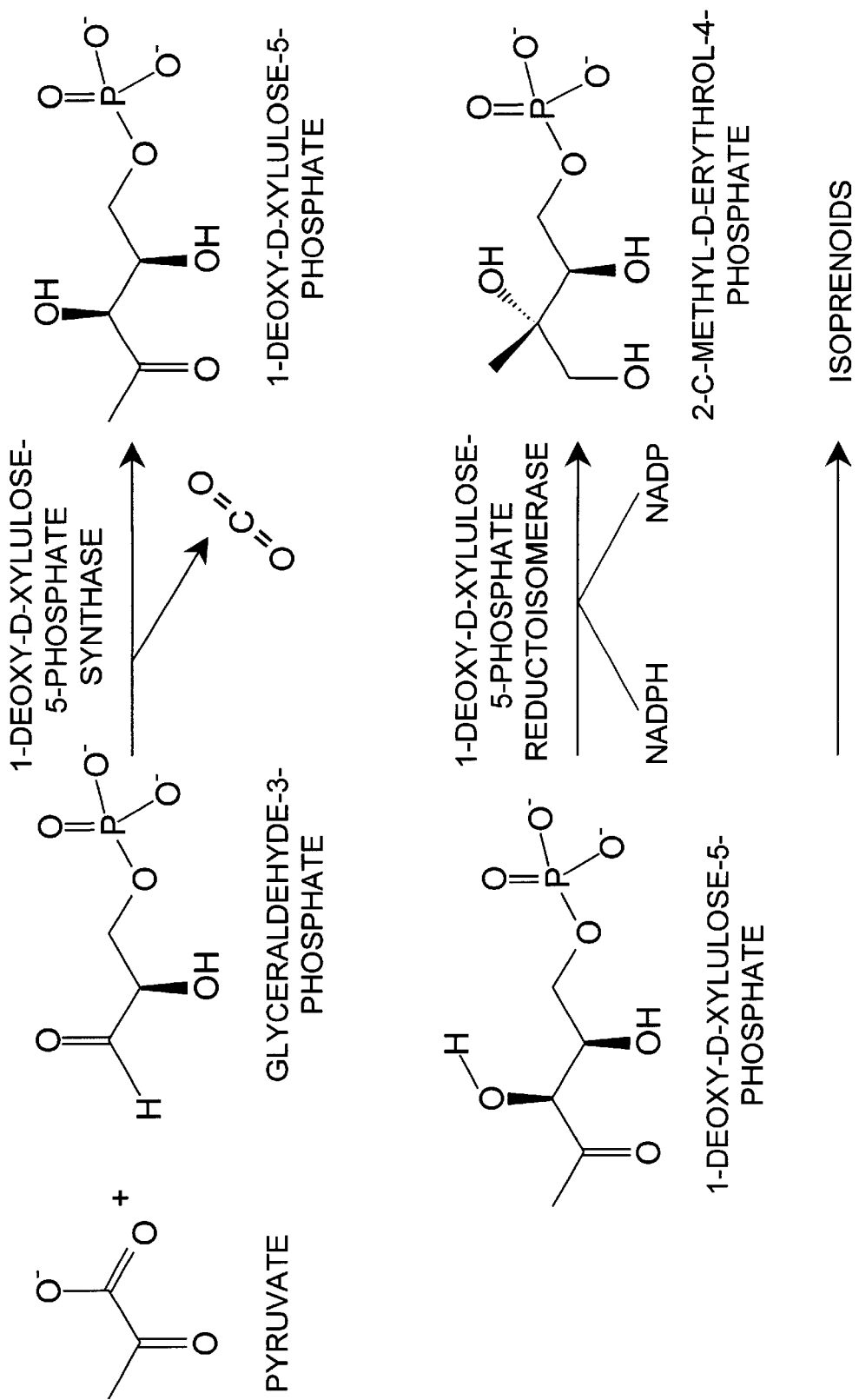

SEQUENCE LISTING

<160> NUMBER OF SEQ ID NOS: 8

<210> SEQ ID NO 1
<211> LENGTH: 1732
<212> TYPE: DNA
<213> ORGANISM: Arabidopsis thaliana

```
<220> FEATURE:
<221> NAME/KEY: CDS
<222> LOCATION: (18)..(1448)
<223> OTHER INFORMATION: DNA encoding 1-deoxy-D-xylulose-5-phosphate
      reductoisomerase

<400> SEQUENCE: 1 tttttaaaa gactctg atg atg aca tta aac tca cta tct cca gct gaa         50
                  Met Met Thr Leu Asn Ser Leu Ser Pro Ala Glu
                   1               5                  10 tcc aaa gct att tct ttc ttg gat acc tcc agg ttc aat cca atc cct       98
Ser Lys Ala Ile Ser Phe Leu Asp Thr Ser Arg Phe Asn Pro Ile Pro
         15                  20                  25 aaa ctc tca ggt ggg ttt agt ttg agg agg agg aat caa ggg aga ggt      146
Lys Leu Ser Gly Gly Phe Ser Leu Arg Arg Arg Asn Gln Gly Arg Gly
 30                  35                  40 ttt gga aaa ggt gtt aag tgt tca gtg aaa gtg cag cag caa caa caa      194
Phe Gly Lys Gly Val Lys Cys Ser Val Lys Val Gln Gln Gln Gln Gln
 45                  50                  55 cct cct cca gca tgg cct ggg aga gct gtc cct gag gcg cct cgt caa      242
Pro Pro Pro Ala Trp Pro Gly Arg Ala Val Pro Glu Ala Pro Arg Gln
 60                  65                  70                  75 tct tgg gat gga cca aaa ccc atc tct atc gtt gga tct act ggt tct      290
Ser Trp Asp Gly Pro Lys Pro Ile Ser Ile Val Gly Ser Thr Gly Ser
                 80                  85                  90 att ggc act cag aca ttg gat att gtg gct gag aat cct gac aaa ttc      338
Ile Gly Thr Gln Thr Leu Asp Ile Val Ala Glu Asn Pro Asp Lys Phe
         95                 100                 105 aga gtt gtg gct cta gct gct ggt tcg aat gtt act cta ctt gct gat      386
Arg Val Val Ala Leu Ala Ala Gly Ser Asn Val Thr Leu Leu Ala Asp
110                 115                 120 cag gta agg aga ttt aag cct gca ttg gtt gct gtt aga aac gag tca      434
Gln Val Arg Arg Phe Lys Pro Ala Leu Val Ala Val Arg Asn Glu Ser
        125                 130                 135 ctg att aat gag ctt aaa gag gct tta gct gat ttg gac tat aaa ctc      482
Leu Ile Asn Glu Leu Lys Glu Ala Leu Ala Asp Leu Asp Tyr Lys Leu
140                 145                 150                 155 gag att att cca gga gag caa gga gtg att gag gtt gcc cga cat cct      530
Glu Ile Ile Pro Gly Glu Gln Gly Val Ile Glu Val Ala Arg His Pro
                160                 165                 170 gaa gct gta acc gtt gtt acc gga ata gta ggt tgt gcg gga cta aag      578
Glu Ala Val Thr Val Val Thr Gly Ile Val Gly Cys Ala Gly Leu Lys
        175                 180                 185 cct acg gtt gct gca att gaa gca gga aag gac att gct ctt gca aac      626
Pro Thr Val Ala Ala Ile Glu Ala Gly Lys Asp Ile Ala Leu Ala Asn
190                 195                 200 aaa gag aca tta atc gca ggt ggt cct ttc gtg ctt ccg ctt gcc aac      674
Lys Glu Thr Leu Ile Ala Gly Gly Pro Phe Val Leu Pro Leu Ala Asn
        205                 210                 215 aaa cat aat gta aag att ctt ccg gca gat tca gaa cat tct gcc ata      722
Lys His Asn Val Lys Ile Leu Pro Ala Asp Ser Glu His Ser Ala Ile
220                 225                 230                 235 ttt cag tgt att caa ggt ttg cct gaa ggc gct ctg cgc aag ata atc      770
Phe Gln Cys Ile Gln Gly Leu Pro Glu Gly Ala Leu Arg Lys Ile Ile
                240                 245                 250 ttg act gca tct ggt gga gct ttt agg gat tgg cct gtc gaa aag cta      818
Leu Thr Ala Ser Gly Gly Ala Phe Arg Asp Trp Pro Val Glu Lys Leu
        255                 260                 265 aag gaa gtt aaa gta gcg gat gcg ttg aag cat cca aac tgg aac atg      866
Lys Glu Val Lys Val Ala Asp Ala Leu Lys His Pro Asn Trp Asn Met
270                 275                 280
```

```
gga aag aaa atc act gtg gac tcc tgt acg ctt ttc aac aag ggt ctt      914
Gly Lys Lys Ile Thr Val Asp Ser Cys Thr Leu Phe Asn Lys Gly Leu
        285                 290                 295 gag gtc att gaa gcg cat tat ttg ttt gga gct gag tat gac gat ata      962
Glu Val Ile Glu Ala His Tyr Leu Phe Gly Ala Glu Tyr Asp Asp Ile
300                 305                 310                 315 gag att gtc att cat ccg caa agt atc ata cat tcc atg att gaa aca     1010
Glu Ile Val Ile His Pro Gln Ser Ile Ile His Ser Met Ile Glu Thr
                320                 325                 330 cag gat tca tct gtg ctt gct caa ttg ggt tgg cct gat atg cgt tta     1058
Gln Asp Ser Ser Val Leu Ala Gln Leu Gly Trp Pro Asp Met Arg Leu
            335                 340                 345 ccg att ctc tac acc atg tca tgg ccc gat aga gtt cct tgt tct gaa     1106
Pro Ile Leu Tyr Thr Met Ser Trp Pro Asp Arg Val Pro Cys Ser Glu
        350                 355                 360 gta act tgg cca aga ctt gac ctt tgc aaa ctc ggt tca ttg act ttc     1154
Val Thr Trp Pro Arg Leu Asp Leu Cys Lys Leu Gly Ser Leu Thr Phe
    365                 370                 375 aag aaa cca gac aat gtg aaa tac cca tcc atg gat ctt gct tat gct     1202
Lys Lys Pro Asp Asn Val Lys Tyr Pro Ser Met Asp Leu Ala Tyr Ala
380                 385                 390                 395 gct gga cga gct gga ggc aca atg act gga gtt ctc agc gcc gcc aat     1250
Ala Gly Arg Ala Gly Gly Thr Met Thr Gly Val Leu Ser Ala Ala Asn
                400                 405                 410 gag aaa gct gtt gaa atg ttc att gat gaa aag ata agc tat ttg gat     1298
Glu Lys Ala Val Glu Met Phe Ile Asp Glu Lys Ile Ser Tyr Leu Asp
            415                 420                 425 atc ttc aag gtt gtg gaa tta aca tgc gat aaa cat cga aac gag ttg     1346
Ile Phe Lys Val Val Glu Leu Thr Cys Asp Lys His Arg Asn Glu Leu
        430                 435                 440 gta aca tca ccg tct ctt gaa gag att gtt cac tat gac ttg tgg gca     1394
Val Thr Ser Pro Ser Leu Glu Glu Ile Val His Tyr Asp Leu Trp Ala
    445                 450                 455 cgt gaa tat gcc gcg aat gtg cag ctt tct tct ggt gct agg cca gtt     1442
Arg Glu Tyr Ala Ala Asn Val Gln Leu Ser Ser Gly Ala Arg Pro Val
460                 465                 470                 475 cat gca tgaagaattg gttgttggaa gaacataagg aagcttctga ggaaatgttg     1498
His Ala aaagaagatt agtgtagaga atggggtact acttaatagc gttttggca aggattatgg    1558 attgtgtagc taatttatct gtgatccgaa caagccaaac tgataatttg aaaccattgt    1618
gatccgaaca agccaaactg ataatttgaa accatttta ccaataaaac cgagcttaat    1678
tgtttcacat tatatgatta attacattca tctaagggtt cttgaaaaaa aaaa         1732

<210> SEQ ID NO 2
<211> LENGTH: 477
<212> TYPE: PRT
<213> ORGANISM: Arabidopsis thaliana

<400> SEQUENCE: 2

Met Met Thr Leu Asn Ser Leu Ser Pro Ala Glu Ser Lys Ala Ile Ser
 1               5                  10                  15

Phe Leu Asp Thr Ser Arg Phe Asn Pro Ile Pro Lys Leu Ser Gly Gly
            20                  25                  30

Phe Ser Leu Arg Arg Arg Asn Gln Gly Arg Gly Phe Gly Lys Gly Val
        35                  40                  45

Lys Cys Ser Val Lys Val Gln Gln Gln Gln Pro Pro Ala Trp
    50                  55                  60
```

-continued

```
Pro Gly Arg Ala Val Pro Glu Ala Pro Arg Gln Ser Trp Asp Gly Pro
 65                  70                  75                  80

Lys Pro Ile Ser Ile Val Gly Ser Thr Gly Ser Ile Gly Thr Gln Thr
                 85                  90                  95

Leu Asp Ile Val Ala Glu Asn Pro Asp Lys Phe Arg Val Val Ala Leu
            100                 105                 110

Ala Ala Gly Ser Asn Val Thr Leu Leu Ala Asp Gln Val Arg Arg Phe
        115                 120                 125

Lys Pro Ala Leu Val Ala Val Arg Asn Glu Ser Leu Ile Asn Glu Leu
130                 135                 140

Lys Glu Ala Leu Ala Asp Leu Asp Tyr Lys Leu Glu Ile Ile Pro Gly
145                 150                 155                 160

Glu Gln Gly Val Ile Glu Val Ala Arg His Pro Glu Ala Val Thr Val
                165                 170                 175

Val Thr Gly Ile Val Gly Cys Ala Gly Leu Lys Pro Thr Val Ala Ala
            180                 185                 190

Ile Glu Ala Gly Lys Asp Ile Ala Leu Ala Asn Lys Glu Thr Leu Ile
        195                 200                 205

Ala Gly Gly Pro Phe Val Leu Pro Leu Ala Asn Lys His Asn Val Lys
    210                 215                 220

Ile Leu Pro Ala Asp Ser Glu His Ser Ala Ile Phe Gln Cys Ile Gln
225                 230                 235                 240

Gly Leu Pro Glu Gly Ala Leu Arg Lys Ile Ile Leu Thr Ala Ser Gly
                245                 250                 255

Gly Ala Phe Arg Asp Trp Pro Val Glu Lys Leu Lys Glu Val Lys Val
            260                 265                 270

Ala Asp Ala Leu Lys His Pro Asn Trp Asn Met Gly Lys Lys Ile Thr
        275                 280                 285

Val Asp Ser Cys Thr Leu Phe Asn Lys Gly Leu Glu Val Ile Glu Ala
    290                 295                 300

His Tyr Leu Phe Gly Ala Glu Tyr Asp Asp Ile Glu Ile Val Ile His
305                 310                 315                 320

Pro Gln Ser Ile Ile His Ser Met Ile Glu Thr Gln Asp Ser Ser Val
                325                 330                 335

Leu Ala Gln Leu Gly Trp Pro Asp Met Arg Leu Pro Ile Leu Tyr Thr
            340                 345                 350

Met Ser Trp Pro Asp Arg Val Pro Cys Ser Glu Val Thr Trp Pro Arg
        355                 360                 365

Leu Asp Leu Cys Lys Leu Gly Ser Leu Thr Phe Lys Lys Pro Asp Asn
370                 375                 380

Val Lys Tyr Pro Ser Met Asp Leu Ala Tyr Ala Ala Gly Arg Ala Gly
385                 390                 395                 400

Gly Thr Met Thr Gly Val Leu Ser Ala Ala Asn Glu Lys Ala Val Glu
                405                 410                 415

Met Phe Ile Asp Glu Lys Ile Ser Tyr Leu Asp Ile Phe Lys Val Val
            420                 425                 430

Glu Leu Thr Cys Asp Lys His Arg Asn Glu Leu Val Thr Ser Pro Ser
        435                 440                 445

Leu Glu Glu Ile Val His Tyr Asp Leu Trp Ala Arg Glu Tyr Ala Ala
    450                 455                 460

Asn Val Gln Leu Ser Ser Gly Ala Arg Pro Val His Ala
465                 470                 475
```

<210> SEQ ID NO 3
<211> LENGTH: 30
<212> TYPE: DNA
<213> ORGANISM: Arabidopsis thaliana

<400> SEQUENCE: 3
cctaggatcc atggcttctt ctgcatttgc                               30

<210> SEQ ID NO 4
<211> LENGTH: 29
<212> TYPE: DNA
<213> ORGANISM: Arabidopsis thaliana

<400> SEQUENCE: 4
atatgcggcc gctcaaaaca gagcttccc                                29

<210> SEQ ID NO 5
<211> LENGTH: 1732
<212> TYPE: DNA
<213> ORGANISM: Arabidopsis thaliana
<220> FEATURE:
<221> NAME/KEY: CDS
<222> LOCATION: (18)..(1448)
<223> OTHER INFORMATION: new coding sequence

<400> SEQUENCE: 5

```
tttttaaaa gactctg atg atg aca tta aac tca cta tct cca gct gaa         50
                 Met Met Thr Leu Asn Ser Leu Ser Pro Ala Glu
                  1               5                  10 tcc aaa gct att tct ttc ttg gat acc tcc agg ttc aat cca atc cct        98
Ser Lys Ala Ile Ser Phe Leu Asp Thr Ser Arg Phe Asn Pro Ile Pro
         15                  20                  25 aaa ctc tca ggt ggg ttt agt ttg agg agg agg aat caa ggg aga ggt       146
Lys Leu Ser Gly Gly Phe Ser Leu Arg Arg Arg Asn Gln Gly Arg Gly
 30                  35                  40 ttt gga aaa ggt gtt aag tgt tca gtg aaa gtg cag cag caa caa caa       194
Phe Gly Lys Gly Val Lys Cys Ser Val Lys Val Gln Gln Gln Gln Gln
     45                  50                  55 cct cct cca gca tgg cct ggg aga gct gtc cct gag gcg cct cgt caa       242
Pro Pro Pro Ala Trp Pro Gly Arg Ala Val Pro Glu Ala Pro Arg Gln
 60                  65                  70                  75 tct tgg gat gga cca aaa ccc atc tct atc gtt gga tct act ggt tct       290
Ser Trp Asp Gly Pro Lys Pro Ile Ser Ile Val Gly Ser Thr Gly Ser
                 80                  85                  90 att ggc act cag aca ttg gat att gtg gct gag aat cct gac aaa ttc       338
Ile Gly Thr Gln Thr Leu Asp Ile Val Ala Glu Asn Pro Asp Lys Phe
         95                 100                 105 aga gtt gtg gct cta gct gct ggt tcg aat gtt act cta ctt gct gat       386
Arg Val Val Ala Leu Ala Ala Gly Ser Asn Val Thr Leu Leu Ala Asp
    110                 115                 120 cag gta agg aga ttt aag cct gca ttg gtt gct gtt aga aac gag tca       434
Gln Val Arg Arg Phe Lys Pro Ala Leu Val Ala Val Arg Asn Glu Ser
125                 130                 135 ctg att aat gag ctt aaa gag gct tta gct gat ttg gac tat aaa ctc       482
Leu Ile Asn Glu Leu Lys Glu Ala Leu Ala Asp Leu Asp Tyr Lys Leu
140                 145                 150                 155 gag att att cca gga gag caa gga gtg att gag gtt gcc cga cat cct       530
Glu Ile Ile Pro Gly Glu Gln Gly Val Ile Glu Val Ala Arg His Pro
                160                 165                 170 gaa gct gta acc gtt gtt acc gga ata gta ggt tgt gcg gga cta aag       578
Glu Ala Val Thr Val Val Thr Gly Ile Val Gly Cys Ala Gly Leu Lys
        175                 180                 185
```

```
cct acg gtt gct gca att gaa gca gga aag gac att gct ctt gca aac   626
Pro Thr Val Ala Ala Ile Glu Ala Gly Lys Asp Ile Ala Leu Ala Asn
        190                 195                 200 aaa gag aca tta atc gca ggt ggt cct ttc gtg ctt ccg ctt gcc aac   674
Lys Glu Thr Leu Ile Ala Gly Gly Pro Phe Val Leu Pro Leu Ala Asn
205                 210                 215 aaa cat aat gta aag att ctt ccg gca gat tca gaa cat tct gcc ata   722
Lys His Asn Val Lys Ile Leu Pro Ala Asp Ser Glu His Ser Ala Ile
220                 225                 230                 235 ttt cag tgt att caa ggt ttg cct gaa ggc gct ctg cgc aag ata atc   770
Phe Gln Cys Ile Gln Gly Leu Pro Glu Gly Ala Leu Arg Lys Ile Ile
                240                 245                 250 ttg act gca tct ggt gga gct ttt agg gat tgg cct gtc gaa aag cta   818
Leu Thr Ala Ser Gly Gly Ala Phe Arg Asp Trp Pro Val Glu Lys Leu
                255                 260                 265 aag gaa gtt aaa gta gcg gat gcg ttg aag cat cca aac tgg aac atg   866
Lys Glu Val Lys Val Ala Asp Ala Leu Lys His Pro Asn Trp Asn Met
                270                 275                 280 gga aag aaa atc act gtg gac tct gct acg ctt ttc aac aag ggt ctt   914
Gly Lys Lys Ile Thr Val Asp Ser Ala Thr Leu Phe Asn Lys Gly Leu
285                 290                 295 gag gtc att gaa gcg cat tat ttg ttt gga gct gag tat gac gat ata   962
Glu Val Ile Glu Ala His Tyr Leu Phe Gly Ala Glu Tyr Asp Asp Ile
300                 305                 310                 315 gag att gtc att cat ccg caa agt atc ata cat tcc atg att gaa aca  1010
Glu Ile Val Ile His Pro Gln Ser Ile Ile His Ser Met Ile Glu Thr
                320                 325                 330 cag gat tca tct gtg ctt gct caa ttg ggt tgg cct gat atg cgt tta  1058
Gln Asp Ser Ser Val Leu Ala Gln Leu Gly Trp Pro Asp Met Arg Leu
                335                 340                 345 ccg att ctc tac acc atg tca tgg ccc gat aga gtt cct tgt tct gaa  1106
Pro Ile Leu Tyr Thr Met Ser Trp Pro Asp Arg Val Pro Cys Ser Glu
                350                 355                 360 gta act tgg cca aga ctt gac ctt tgc aaa ctc ggt tca ttg act ttc  1154
Val Thr Trp Pro Arg Leu Asp Leu Cys Lys Leu Gly Ser Leu Thr Phe
365                 370                 375 aag aaa cca gac aat gtg aaa tac cca tcc atg gat ctt gct tat gct  1202
Lys Lys Pro Asp Asn Val Lys Tyr Pro Ser Met Asp Leu Ala Tyr Ala
380                 385                 390                 395 gct gga cga gct gga ggc aca atg act gga gtt ctc agc gcc gcc aat  1250
Ala Gly Arg Ala Gly Gly Thr Met Thr Gly Val Leu Ser Ala Ala Asn
                400                 405                 410 gag aaa gct gtt gaa atg ttc att gat gaa aag ata agc tat ttg gat  1298
Glu Lys Ala Val Glu Met Phe Ile Asp Glu Lys Ile Ser Tyr Leu Asp
                415                 420                 425 atc ttc aag gtt gtg gaa tta aca tgc gat aaa cat cga aac gag ttg  1346
Ile Phe Lys Val Val Glu Leu Thr Cys Asp Lys His Arg Asn Glu Leu
                430                 435                 440 gta aca tca ccg tct ctt gaa gag att gtt cac tat gac ttg tgg gca  1394
Val Thr Ser Pro Ser Leu Glu Glu Ile Val His Tyr Asp Leu Trp Ala
                445                 450                 455 cgt gaa tat gcc gcg aat gtg cag ctt tct tct ggt gct agg cca gtt  1442
Arg Glu Tyr Ala Ala Asn Val Gln Leu Ser Ser Gly Ala Arg Pro Val
460                 465                 470                 475 cat gca tgaagaattg gttgttggaa gaacataagg aagcttctga ggaaatgttg   1498
His Ala aaagaagatt agtgtagaga atgggtact acttaatagc gttttttggca aggattatgg  1558 attgtgtagc taatttatct gtgatccgaa caagccaaac tgataatttg aaaccattgt   1618
```

```
gatccgaaca agccaaactg ataatttgaa accatttta ccaataaaac cgagcttaat      1678
tgtttcacat tatatgatta attacattca tctaagggtt cttgaaaaaa aaaa           1732
```

<210> SEQ ID NO 6
<211> LENGTH: 477
<212> TYPE: PRT
<213> ORGANISM: Arabidopsis thaliana

<400> SEQUENCE: 6

```
Met Met Thr Leu Asn Ser Leu Ser Pro Ala Glu Ser Lys Ala Ile Ser
 1               5                   10                  15

Phe Leu Asp Thr Ser Arg Phe Asn Pro Ile Pro Lys Leu Ser Gly Gly
                20                  25                  30

Phe Ser Leu Arg Arg Arg Asn Gln Gly Arg Gly Phe Gly Lys Gly Val
            35                  40                  45

Lys Cys Ser Val Lys Val Gln Gln Gln Gln Pro Pro Pro Ala Trp
        50                  55                  60

Pro Gly Arg Ala Val Pro Glu Ala Pro Arg Gln Ser Trp Asp Gly Pro
 65                  70                  75                  80

Lys Pro Ile Ser Ile Val Gly Ser Thr Gly Ser Ile Gly Thr Gln Thr
                85                  90                  95

Leu Asp Ile Val Ala Glu Asn Pro Asp Lys Phe Arg Val Val Ala Leu
                100                 105                 110

Ala Ala Gly Ser Asn Val Thr Leu Leu Ala Asp Gln Val Arg Arg Phe
            115                 120                 125

Lys Pro Ala Leu Val Ala Val Arg Asn Glu Ser Leu Ile Asn Glu Leu
        130                 135                 140

Lys Glu Ala Leu Ala Asp Leu Asp Tyr Lys Leu Glu Ile Ile Pro Gly
145                 150                 155                 160

Glu Gln Gly Val Ile Glu Val Ala Arg His Pro Glu Ala Val Thr Val
                165                 170                 175

Val Thr Gly Ile Val Gly Cys Ala Gly Leu Lys Pro Thr Val Ala Ala
                180                 185                 190

Ile Glu Ala Gly Lys Asp Ile Ala Leu Ala Asn Lys Glu Thr Leu Ile
            195                 200                 205

Ala Gly Gly Pro Phe Val Leu Pro Leu Ala Asn Lys His Asn Val Lys
        210                 215                 220

Ile Leu Pro Ala Asp Ser Glu His Ser Ala Ile Phe Gln Cys Ile Gln
225                 230                 235                 240

Gly Leu Pro Glu Gly Ala Leu Arg Lys Ile Ile Leu Thr Ala Ser Gly
                245                 250                 255

Gly Ala Phe Arg Asp Trp Pro Val Glu Lys Leu Lys Glu Val Lys Val
                260                 265                 270

Ala Asp Ala Leu Lys His Pro Asn Trp Asn Met Gly Lys Lys Ile Thr
        275                 280                 285

Val Asp Ser Ala Thr Leu Phe Asn Lys Gly Leu Glu Val Ile Glu Ala
        290                 295                 300

His Tyr Leu Phe Gly Ala Glu Tyr Asp Asp Ile Glu Ile Val Ile His
305                 310                 315                 320

Pro Gln Ser Ile Ile His Ser Met Ile Glu Thr Gln Asp Ser Ser Val
                325                 330                 335

Leu Ala Gln Leu Gly Trp Pro Asp Met Arg Leu Pro Ile Leu Tyr Thr
                340                 345                 350
```

```
Met Ser Trp Pro Asp Arg Val Pro Cys Ser Glu Val Thr Trp Pro Arg
        355                 360                 365

Leu Asp Leu Cys Lys Leu Gly Ser Leu Thr Phe Lys Lys Pro Asp Asn
        370                 375                 380

Val Lys Tyr Pro Ser Met Asp Leu Ala Tyr Ala Ala Gly Arg Ala Gly
385                 390                 395                 400

Gly Thr Met Thr Gly Val Leu Ser Ala Ala Asn Glu Lys Ala Val Glu
                405                 410                 415

Met Phe Ile Asp Glu Lys Ile Ser Tyr Leu Asp Ile Phe Lys Val Val
                420                 425                 430

Glu Leu Thr Cys Asp Lys His Arg Asn Glu Leu Val Thr Ser Pro Ser
        435                 440                 445

Leu Glu Glu Ile Val His Tyr Asp Leu Trp Ala Arg Glu Tyr Ala Ala
        450                 455                 460

Asn Val Gln Leu Ser Ser Gly Ala Arg Pro Val His Ala
465                 470                 475

<210> SEQ ID NO 7
<211> LENGTH: 32
<212> TYPE: DNA
<213> ORGANISM: Arabidopsis thaliana

<400> SEQUENCE: 7
cctagaattc atgacattaa actcactatc tc                                      32

<210> SEQ ID NO 8
<211> LENGTH: 30
<212> TYPE: DNA
<213> ORGANISM: Arabidopsis thaliana

<400> SEQUENCE: 8
atatgtcgac tcatgcatga actggcctag                                         30
```

METHOD OF DETERMINING ACTIVITY OF 1-DEOXY-D-XYLULOSE-5-PHOSPHATE REDUCTOISOMERASE AND 1-DEOXY-D-XYLULOSE-5-PHOSPHATE SYNTHASE

The invention relates to DNA which encodes for Arabidopsis 1-deoxy-D-xylulose-5 phosphate reductoisomerase, and to a method of identifying modulators of an enzyme with 1-deoxy-D-xylulose-5-phosphate reductoisomerase activity and of an enzyme with 1-deoxy-D-xylulose-5-phosphate synthase activity.

Undesired vegetation can be prevented by using herbicides. The demands made of herbicides have risen constantly with regard to activity, costs and ecofriendliness. There is therefore a need for new substances which can be developed into new potent herbicides. In general, it is normal to search for such new guide structures in greenhouse tests. However, such tests are laborious and expensive. The number of substances which can be tested in the greenhouse is, accordingly, limited.

The search is underway for plant-specific biosynthetic routes which constitute advantageous sites of action for herbicides and do not occur in animal organisms.

Recently, it has been found that plants synthesize essential plastid isoprenoids not by exploiting the mevalonate biosynthetic pathway which is found in the animal organism, but the microbial 1-deoxy-xylulose-5-phosphate biosynthetic pathway (Lichtenthaler, K. (1998), Fett/Lipid 100, 128–138; Eisenreich et al). (1998), Chemistry & Biology 5, R221–R233).

This biosynthetic pathway finally leads to the synthesis of, inter alia, carotenoids: and the side chains of plastoquinone and chlorophyll. These products are essential for the photosynthetic growth of plants, Inhibition of one step in this biosynthetic pathway entails the end of plant growth.

This is why the 1-deoxy-xylulose-5-phosphate biosynthetic pathway is of particular interest in the search for new herbicidally active compounds. In particular the two enzymes 1-deoxy-D-xylulose-5-phosphate synthase (DXPS) and 1-deoxy-D xylulose-5-phosphate reductoisomerase (DXPR) are of central importance. It has already been demonstrated that DXPS (CLA I) is essential for the development of a normal plant (Mandel et al. (1996), Plant J. 9, 649–658). This discovery supports the expectation that a herbicidal compound which affects DXPS activity has a herbicidal action. Also, it has been demonstrated that bacterial DXFR is inhibited by the herbicidal compound Fosmidomycin, which is already known (Zeidler et al. (1998), Z. Naturforsch. 53, 980–986; Kuzuyama et al. (1998), Tetrahedron Lett. 39, 7913–7916). However, there are no commercially useable herbicides, which affect DXPS or DXPR activity. In the search for new, improved herbicides, both enzymes are therefore of high importance as sites of action. The 1-deoxy-xylulose-5-phosphate biosynthetic pathway also has importance in microorganisms, especially in parasitic microorganisms as, for example, bacteria or plasmodia. The treatment of infectious diseases, in particular the treatment of malaria, may be based on the inhibition of this metabolic pathway (Jomaa et al. (1999), Science 285, 1573–1576).

So far it has not been possible to determine the enzymatic activity of the enzyme 1-deoxy-xylulose-5-phosphate synthase in a simple test system since the reaction neither entails a measurable change in absorption nor can be coupled in a simple manner with a colour change or fluorescence change (FIG. 1). The enzymatic activity of 1-deoxy-D-xylulose-5-phosphate reductoisomerase entails a measurable change in the optical absorption of the cosubstrate NADPH. However the substrate 1-deoxy-D-xylulose-5-phosphate can only be synthesized with difficulty (FIG. 1). While 1-deoxy-D-xylulose-5-phosphate can be prepared via a chemical or biochemical route, both methods are expensive and are not well suited for use in test systems with high throughput (Taylor et al. (1998), J. Org. Chem. 63, 2375–2377; Blagg and Poulter (1999), J. Org. Chem. 64, 1508–1511).

The present invention solves these problems by combining the two enzymes in one test system. The *Arabidopsis thaliana* 1-deoxy-D-xylulose-5-phosphate synthase gene is already known under the name CLAI (Mandel et al. (1996), Plant J.5. 649–658). The 1-deoxy-D-xylulose-5-phosphate reductoisomerase gene is, as yet, known only from *Mentha piperita* (Lange et al. (1998), Proc. Nati. Acad. Sci. U.S.A. 5, 2100–2104) and from various microorganisms. The *A. thaliana* 1-deoxy-D-xylulose-5-phosphate reductoisomerase has also been described and a fragment of the amino acid sequence has been published (Lange und Croteau (1999). Archives of Biochem. and Biophys. 365, 170–174). The combined reaction of pyruvate and glyceraldehyde-3-phosphate to give 2-C-methyl-D-erythrol-4-phosphate is monitored by visually detecting the NADPH consumption (FIG. 1). The test system is suitable for the search for modulators of both enzymes, that is to say substances which inhibit or else stimulate the activity of the enzymes, and can be used for test series with high throughput (high-throughput screening, HTS). After detection of modulators by one of the two enzymes in an HTS system, the modulators of the two enzymes can be distinguished from each other by using the existing methods for measuring the activity of the two enzymes (Sprenger et al. (1997), Proc. Natl. Acad. Sci. U.S.A. 94, 12857–12862; Kuzuyama et al. (1998), Tetrahedron Lett. 39, 4509–4512; DE 197 52 700-A1).

The present invention relates to the DNA which encodes Arabidopsis 1-deoxy-D xylulose-5-phosphate reductoisomerase, in particular the *Arabidopsis thaliana* 1-deoxy-D-xylulose-5-phosphate reductoisomerase, and to fragments of this DNA, which encode functional subunits of 1-deoxy-D-xylulose-5-phosphate reductoisomerase.

The invention furthermore relates to DNA which encodes Arabidopsis 1-deoxy-D-xylulose-5-phosphate reductoisomerase, with an amino acid sequence as shown in SEQ ID NO 2or SEQ ID NO 6.

The invention furthermore relates to DNA as described under SEQ ID NO 1 or SEQ ID NO 5 which encodes the *Arabidopsis thaliana* 1-deoxy-D-xylulose-5-phosphate reductoisomerase.

The invention furthermore relates to DNA which shows 80%, preferably 90%, homology to the DNA described under SEQ ID NO 1 or SEQ ID NO 5 and which encodes plant 1-deoxy-D-xylulose-5-phosphate reductoisomerase.

The invention furthermore relates to DNA which is complementary to the DNA which encodes the *Arabidopsis thaliana* 1-deoxy-D-xylulose-5-phosphate reductoisomerase, and to RNA which is complementary to the DNA which encodes the *Arabidopsis thaliana* 1-deoxy-D-xylulose-5-phosphate reductoisomerase.

The invention furthermore relates to an expression construct which encompasses DNA which encodes the *Arabidopsis thaliana* 1-deoxy-D-xylulose-5-phosphate reductoisomerase and is described under SEQ ID NO 1 or SEQ ID NO 5, and to a sequence which is functionally linked herewith and which allows the 1-deoxy-D-xylulose-5-phosphate reductoisomerase to be expressed.

The invention furthermore relates to a vector which comprises DNA which encodes the *Arabidopsis thaliana*

1-deoxy-D-xylulose-5-phosphate reductoisomerase and/or is described under SEQ ID NO 1 or SEQ ID NO 5 and which allows the 1-deoxy-D-xylulose-5-phosphate reductoisomerase to be expressed in a host cell.

The invention furthermore relates to a host cell which comprises the abovementioned DNA, an expression construct as mentioned above, or a vector which allows the 1-deoxy-D-xylulose-5-phosphate reductoisomerase to be expressed.

The invention furthermore relates to the use of DXPR and/or DXPS modulators as herbicides, antibiotic agents or anti-malarial agents.

The invention also relates to the use of DXPR and/or DXPS modulators as lead structures for the chemical optimization and the development of improved modulators.

The invention also relates to a method of determining the activity of 1-deoxy-D-xylulose-5-phosphate reductoisomerase and 1-deoxy-D-xylulose-5-phosphate synthase, which is based on combining the conversion of pyruvate and glyceraldehyde-3-phosphate to give I -deoxy-D-xylulose-5-phosphate by 1-deoxy-D-xylulose-5-phosphate synthase with the conversion of the resulting 1-deoxy-D-xylulose-5-phosphate to give 2-C-methyl-D-erythrol-4-phosphate by 1-deoxy-D-xylulose-5-phosphate reductoisomerase in one test system.

The course of the overall reaction, that is to say the conversion of the pyruvate and glyceraidehyde-3-phosphate into 2-C-methyl-D-erythrol4-phosphate is monitored with reference to the optical change by the decrease in the cofactor NADPH of 1-deoxy-D-xylulose-5-phosphate reductoisomerase.

The invention also relates to a method of identifying of substances which modify the activity of 1-deoxy-D-xylulose-5-phosphate reductoisomerase or 1-deoxy-D xylulose-5-phosphate synthase, in which the above-described test system for determining the activity of 1-deoxy-D-xylulose-5-phosphate reductoisomerase and of 1 -deoxy-D-xylulose-5-phosphate synthase is used. The test system is optimized in such a way that an optimal conversion of pyruvate and glycer-aldehyde-3-phosphate to give 2-C-methyl-D-erythrol-4-phosphate is ensured. The reaction can be carried out in the presence and absence of substances which modify the activity of one of the enzymes involved. A comparison of the reaction in the presence and absence of such a substance with reference to the NADPH consumption thus allows substances which modulate, preferably inhibit, the activity of 1-deoxy-D-xylulose-5-phosphate reductoisomerase and/or of 1-deoxy-D-xylulose-5-phosphate synthase to be identified.

The invention also relates to substances which are found with the aid of the above described method, with the exception of Fosmidomycin, which is already known to inhibit 1-deoxy-D-xylulose-5-phosphate reductoisomerase (Zeidler et al. (1998), Z. Naturforsch. 53, 980–986).

The invention also relates to the use of substances which are found with the aid of the above-described method for use as modulators, preferably as inhibitors, of the enzymatic activity of 1-deoxy-D-xylulose-5-phosphate reductoisomerase and/or of 1-deoxy-D-xylulose-5-phosphate synthase.

The invention also relates to the use of substances which are found with the aid of the above-described method for use as herbicides, antibiotic agents or anti-malarial agents.

The term "functional fragments" describes those DNA fragments which encode polypeptides which still have 1-deoxy-D-xylulose-5-phosphate reductoisomerase activity, or fragments of 1-deoxy-D-xylulose-5-phosphate reductoisomerase which still have this activity.

The term "homology" in relation to DNA means that DNA segments which are at least 15 base pairs long or strands which are complementary to the DNA match the corresponding DNA in at least 80%, preferably in 90%, of the nucleotides. Such a homology is determined, inter alia, with the aid of computer programs such as the GCG program (Devereux et al. (1983), Nucleic Acids Res. 12, 387–395).

"Homology" exists also when a DNA segment is capable of hybridizing with the DNA strand in question or with its complementary strand.

The term "to hybridize" or "hybridization" describes the process in which a single stranded nucleic acid molecule undergoes base pairing with a complementary DNA strand, where the capability of a single-stranded nucleic acid molecule depends on the stringency of the hybridization conditions.

The term "stringency" relates to the hybridization conditions. "High stringency makes base pairing difficult. To do this, high temperatures of 42° C. or less are used, a formamide concentration of less than 20% and low salt (SSC) concentrations, Alternatively, temperatures of 65° C. or less can be used in combination with a low salt concentration (SSPE). "Low stringency" conditions favour the formation of base pairs. The temperatures used here are 37° C. or less, the formamide concentration is less than 50%, and the salt concentration (SSC) is moderate. Alternatively, temperatures of 50° C. or less in combination with a medium to high salt concentration (SSPE) are used.

The term "complementary" relates to the capability of purine and pyrimidine nucleotides to form base pairs with each other via hydrogen bonds. Complementary base pairs are, inter alia, guanine und cytosine, adenine and thymine, and adenine and uracil.

The term "plasmid" refers to an extrachromosomal genetic element. The original plasmids used for the present invention are either commercially available or freely accessible or can be derived from such plasmids by known methods.

The term "vector" describes a DNA element used for introducing exogenous DNA into host cells. A vector contains a nucleotide sequence which encodes one or more polypeptides.

One skilled in the art is aware of the fact that the degenerate genetic code (i.e. 64 codons encode 20 amino acids) allow a large number of "silent" substitutions of nucleotide base pairs to be introduced into the sequence shown here without changing the identity of the protein products encoded by it. The scope of the invention includes all such substitutions.

DNA Isolation

The nucleic acid mentioned here can exist in complete cells, in cell lysates, in partially purified or biologically pure form, i.e. when other cell components or chemical precursors and by-products, in the case of chemical DNA synthesis, have been removed.

The DNA mentioned here can be obtained by a series of genetic and recombinant DNA techniques, for example by means of amplification with the aid of the polymerase chain reaction (PCR) or else by de novo DNA synthesis. The DNA mentioned here can be isolated by means of PCR amplification of genomic DNA from suitable plant cells using oligonucleotide primers which are directed at a suitable region of SEQ ID NO 1 or SEQ ID NO 5 (see, for example, J. Sambrook et al, (1989), Molecular Cloning, 2nd edition, chapter 14).

Obtaining and Purifying the Protein

The invention also relates to polypeptides which have 1-deoxy-D-xylulose-5 phosphate reductoisomerase activity and which are encoded by an above-described DNA.

The skilled worker knows that the polypeptides of the present invention can be obtained by various routes, for example by chemical methods such as the solid-phase method. To obtain larger quantities of protein, the use of recombinant methods is recommended. Expression of a cloned 1-deoxy-D-xylulose-5-phosphate reductoisomerase gene or fragments thereof can take place in a series of suitable host cells which are known to the skilled worker. To this end, a 1-deoxy-D-xylulose-5 phosphate reductoisomerase gene is introduced into a host cell with the aid of known methods.

The integration of the cloned 1-deoxy-D-xylulose-5-phosphate reductoisomerase gene in the chromosome of the host cell is within the scope of the present invention. Preferably, the gene or fragments thereof are inserted into a plasmid, and the encoding regions of the 1-deoxy-D-xylulose-5-phosphate reductoisomerase gene or fragments thereof are functionally linked to a constitutive or inducible promoter.

The basic steps for generating the recombinant 1-deoxy-D-xylulose-5-phosphate reductoisomerase are:
1. Obtaining a natural, synthetic or semi-synthetic DNA which encodes 1-deoxy D-xylulose-5-phosphate reductoisomerase.
2. Introducing this DNA into an expression vector which is suitable for expressing 1-deoxy-D-xylulose-5-phosphate reductoisomerase either alone or as a fused protein.
3. Transformation of a suitable host cell, preferably a prokaryotic host cell, with this expression vector.
4. Growing this transformed host cell in a manner which is suitable for expressing 1-deoxy-D-xylulose-5-phosphate reductoisomerase.
5. Harvesting the cells and purifying 1-deoxy-D-xylulose-5-phosphate reductoisomerase by suitable known methods.

The encoding regions of 1-deoxy-D-xylulose-5-phosphate reductoisomerase and of 1-deoxy-D-xylulose-5-phosphate synthase can be expressed by the customary methods in *E. coli*, either separately or together. Suitable expression systems for *E. coli* are commercially available, for example the expression vectors of the pET series, for example pET3a, pET23a, pET28a with his-Tag or pET32a with his-Tag for the simple purification and thioredoxin fusion for improving the solubility of the expressed enzyme, a nd pGEX with glutathion synthetase fusion. The expression vectors are transformed into XDE3-lysogenic *E. coli* strains, for example, BL21(DE3), HMS 174(DE3) or AD494 (DE3). After the cells have become attached, expression is induced with IPTG under standard conditions known to the skilled worker. After cell induction, incubation is carried out for 3 to 24 hours at temperatures from 18° C. to 37° C. The cells are disrupted by sonication in disruption buffer (10 to 200 mM sodium phosphate, 100 to 500 mM NaCl, pH 5 to 8). The protein which has been expressed can be purified by chromatographic methods, in the case of protein which has been expressed with a his-Tag by means of chromatography on an Ni-NTA column.

Since, according to current knowledge, the 1-deoxy-xylulose-5-phosphate pathway does not exist in animals and yeasts, expression of the protein in commercially available yeast strains (for example *Pichia pastoris*) or in insect cell cultures (for example Sf9 cells) is another favourable option.

Alternatively, the proteins may also be expressed in plants.
Determination of the 1-deoxy-D-xylulose-5-phosphate Reductoisomerase and/or 1-deoxy-D-xylulose-5-phosphate Synthase Activity, and Identification of Modulators of the Enzyme Activity of Both Enzymes To identify and develop herbicidally active substances, it is necessary to find a way of determining the effect of various candidate substances on 1-deoxy-D-xylulose-5-phosphate reductoisomerase and 1-deoxy-D-xylulose-5-phosphate synthase activity. To this end, a way must be found of measuring the activity of both enzymes in an efficient and simple manner, or of detecting an inhbition or else stimulation of this activity.

One way of determining the effect of a substance on the enzymatic reaction of 1-deoxy-D-xylulose-5-phosphate reductoisomerase and/or of 1-deoxy-D-xylulose-5 phosphate synthase is to contact purified 1-deoxy-D-xylulose-5-phosphate reductoisomerase and 1-deoxy-D-xylulose-5-phosphate synthase, or fragments with 1-deoxy-D-xylulose-5-phosphate reductoisomerase activity and fragments with 1-deoxy-D-xylulose-5-phosphate synthase activity, with a test substance and to check the activity of both enzymes.

According to the present invention, the 1-deoxy-D-xylulose-5-phosphate reductoisomerase and 1-deoxy-D-xylulose-5-phosphate synthase activity is determined in a combined test system which contains both 1-deoxy-D-xylulose-5 phosphate reductoisomerase and 1-deoxy-D-xylulose-5-phosphate synthase. In this test system, 1-deoxy-D-xylulose-5-phosphate synthase converts pyruvate and glyceraidehyde-3-phosphate into 1-deoxy-D-xylulose-5-phosphate, which is converted by 1-deoxy-D-xylulose-5-phosphate reductoisomerase directly into 2-C-methyl-D-erythrol-4-phosphate, with consumption of NADPH. The decrease in the NADPH concentration can be monitored with aid of optical measurement methods (FIG. 1).

To test for substances which modulate, preferably inhibit, the 1-deoxy-D-xylulose-5-phosphate reductoisomerase and/or 1-deoxy-D-xylulose-5-phosphate synthase activity, the test system and the enzyme concentrations are designed in such a way that an optimal conversion of the pyruvate and glyceraldehyde-3-phosphate to give 2-C-methyl-D-Erythrol-4-phosphate is ensured. If one of the enzymes involved is inhibited or activated by a candidate substance, this can be detected by a drop or increase in the NADPH conversion.

Then, a separate activity test for 1-deoxy-D-xylulose-5-phosphate reductoisomerase or 1-deoxy-D-xylulose-5-phosphate synthase may be carried out in the known manner in order to determine which of the two enzymes is affected in its activity by the substance which has been found.

As an alternative to the known, separate activity tests, HPLC makes it possible to determine, starting from the combined activity test, which products or intermediates starting from the materials pyruvate and glyceraldehyde-3-phosphate have been formed. If 1-deoxy-D-xylulose-5-phosphate has been formed, but not 2-C-methyl-D erythrol-4-phosphate, then it was DXPR which was inhibited. If 1-deoxy-D-xylulose-5-phosphate has not been formed either, the DXPS was (also) inhibited.

EXAMPLE 1

Construction of a Vector for Expressing the *Arabidopsis thaliana* 1-deoxy-D-xululose-5-phosphate Synthase The encoding sequence of the *Arabidopsis thaliana* CLA1 gene from position +1 to +2154 was amplified with the aid of the PCR technique using the following primers of the sequences shown in SEQ ID NO. 3 and SEQ ID NO. 4 (Mandel et al. (1996) CLAI, a novel gene required for chloroplast development, is highly conserved in evolution; Plant J. 5 649–658; Lange M. et al. (1998) A family of transketolases that directs isoprenoid biosynthesis via a mevalonate-independant pathway; Proc. Natl. Acad. Sci, U.S.A. 95, 2100–2104).

The template used was *Arabidopsis thaliana* single-stranded cDNA from 4-week-old seedlings.

The amplified fragment which carries the encoding sequence of the *Arabidopsis thaliana* DXPS was then cleaved with the restriction enzymes BamHI and NotI. The resulting BamHI/NotI-DXPS fragment was ligated into the linearized and dephosphorylated bacterial expression vector pET32 a (+) (Novagen). The resulting construct pET32-DXPS contains the encoding DXPS sequence within the reading frame with a fragment of the bacterial thioredoxin gene.

EXAMPLE 2

Construction of a Vector for Expressing the *Arabidopsis thaliana* 1-deoxy-D-xylulose-5-phosphate Reductoisomerase The encoding sequence of the *Arabidopsis thaliana* 1-deoxy-D-xylulose-5-phosphate reductoisomerase was amplified with the aid of the PCR technique using the primers with the sequences as shown in SEQ ID NO. 3 and SEQ ID NO. 4. The amplified fragment was then cleaved with the restriction endonucleases EcoRI and SalI. The resulting EcoRI/SalI-DXR fragment was ligated into the linearized and dephosphorylated bacterial expression vector pET32 a (+) (Novagen). In the resulting construct pET32-DXR the encoding DXR sequence was within the reading frame together with a fragment of the bacterial thioredoxin gene.

EXAMPLE 3

Test system for Identifying 1-deoxy-D-xylulose-5-phosphate Reductoisomerase and/or 1-deoxy-D-xylulose-5-phosphate Synthase Modulators in an HTS A microtitre plate (96-well format) is filled with solutions of 1-deoxy-xylulose-5 phosphate synthase (0.1–10 μg of purified enzyme/100 μl) and 1-deoxy-xylulose-5 phosphate reductoisomerase (0.1–10 μg of purified enzyme/100 μl) and of the cosubstrate NADPH (0.1–10 mM) in the customary buffer (10–200 mM sodium phosphate pH 5–8), containing thiamine diphosphate (0.1–10 mM) and $MgCl_2$ (0.5–50 mM). All concentrations (also those given further below) are based on the concentration after addition of all assay components. The candidate chemical, or as control, buffer, is pipetted into each cavity of the microtitre plate. After addition of the substrates pyruvate (1–100 mM) and glyceraldehyde-3-phosphate (1–100 mM) in customary buffer (as above, but without NADPH and without thiamine diphosphate), the plates are incubated between 18° C. and 45° C. until a drop in the optical density of NADPH at 340 nm which can be measured easily has been reached. The optical density is then read in a customary microtitre plate reader. Substances which inhibit one of the two enzymes which participate are identified by a reduced drop of the NADPH concentration with the aid of the optical density measurement.

In microtitre plates of greater density (384-well, 1536-well format and the like), the volumes indicated above are adapted to suit the system.

Explanation of the Figure and of the Sequence Data

FIG. I shows the conversion of pyruvate and glyceraldehyde-3-phosphate via 1-deoxy-D-xylulose-5-phosphate to give 2-C-methyl-D-erythrol-4-phosphate, which is catalysed by the enzymes 1-deoxy-D-xylulose-5-phosphate synthase and 1-deoxy D-xylulose-5-phosphate reductoisomerase. The reaction which is catalysed by 1-deoxy-D-xylulose-5-phosphate reductoisomerase requires NADPH as cofactor. The catalysed reactions are essential for the isoprenoid synthesis in plants.

SEQ ID NO. 1

DNA sequence encoding the *Arabidopsis thaliana* 1-deoxy-D-xylulose-5-phosphate reductoisomerase. The other sequence shown is the amino acid sequence encoded by the DNA.

SEQ ID NO. 2

Amino acid sequence of the *Arabidopsis thaliana* 1-deoxy-D-xylulose-5-phosphate reductoisomerase with 477 amino acids.

SEQ ID NO. 3

Oligonucleotide derived from the encoding sequence of the *Arabidopsis thaliana* CLAI gene for amplifying the *Arabidopsis thaliana* CLA1 gene by means of the PCR technique, including nucleotides for a BamH1 cloning site.

SEQ ID NO. 4

Oligonucleotide derived from the encoding sequence of the *Arabidopsis thaliana* CLAI gene for amplifying the *Arabidopsis thaliana* CLAI gene by means of the PCR technique, including nucleotides for a NotI cloning site.

SEQ ID NO. 5

Another DNA sequence encoding the *Arabidopsis thaliana* 1-deoxy-D-xylulose-5-phosphate reductoisomerase. Change at nucleotides 890–892. The other sequence shown is the amino acid sequence encoded by the DNA.

SEQ ID NO. 6

Another amino acid sequence of the *Arabidopsis thaliana* 1-deoxy-D-xylulose-5-phosphate reductoisomerase with 477 amino acids. Change at amino acid 292.

SEQ ID NO. 7

Oligonucleotide derived from the encoding sequence of the *Arabidopsis thaliana* 1-deoxy-D-xylulose-5-phosphate reductoisomerase gene for amplifying the *Arabidopsis thaliana* 1-deoxy-D-xylulose-5-phosphate reductoisomerase gene by means of the PCR technique.

SEQ ID NO. 8

Oligonucleotide derived from the encoding sequence of the *Arabidopsis thaliana* 1-deoxy-D-xylulose-5-phosphate reductoisomerase gene for amplifying the *Arabidopsis thaliana* 1-deoxy-D-xylulose-5-phosphate reductoi somerase gene by means of the PCR technique.

What is claimed is:

1. An isolated DNA comprising a nucleic acid which encodes an Arabidopsis 1-deoxy-D-xylulose-5-phosphate reductoisomerase that has the amino acid sequence of SEQ ID NO: 6.

2. The DNA according to claim 1, wherein said 1-deoxy-D-xylulose-5-phosphate reductoisomerase is from *Arabidopsis thaliana*.

3. The DNA of claim 1 wherein said DNA comprises the nucleic acid of SEQ ID NO: 5.

4. An isolated DNA that is complementary to the DNA according to any of claims 1, 2 and 3.

5. An isolated RNA that is complementary to the DNA according to any of claims 1, 2 and 3.

6. An expression construct, comprising a DNA according to any of claims 1, 2 and 3, wherein said DNA is functionally linked to a promoter.

7. A vector comprising a DNA according to any of claims 1, 2 and 3.

8. A host cell comprising a DNA according to any of claims 1, 2 and 3.

9. A vector comprising a DNA according to claim 4.

10. A vector comprising a DNA according to claim 6.

11. A host cell comprising a DNA according to claim 4.

12. A host cell comprising an expression construct according to claim 6.

13. A host cell comprising a vector according to claim 7.

* * * * *

Adverse Decision In Interference

Patent No. 6,303,365, William Frank. Martin, Ruediger Hain, Klaus-Guenther Tietjen, Marco Busch, Andreas S. Kloti, METHOD OF DETERMINING ACTIVITY OF 1-DEOXY-D-XYLULOSE-5-PHOSPHATE REDUCTOISOMERASE AND 1-DEOXY-D-XYLULOSE-5-PHOSPHATE SYNTHASE, Interference No. 105,300, final judgment adverse to the patentees rendered May 27, 2005, as to claims 1, 2 and 4-13.

*(Official Gazette, November 22, 2005)*